United States Patent [19]
Korf et al.

[11] Patent Number: 5,782,754
[45] Date of Patent: Jul. 21, 1998

[54] NON-INVASIVE MONITORING OF A CONSTITUENT OF A PHYSIOLOGICAL FLUID

[76] Inventors: Jakob Korf, Houtwallen 11, Vriea, Netherlands, 9481 ER; Jaep de Boer, Ludemaborg 32, Groningen, Netherlands, 9722 WE

[21] Appl. No.: 318,840
[22] PCT Filed: Apr. 22, 1993
[86] PCT No.: PCT/NL93/00086
  § 371 Date: Mar. 23, 1995
  § 102(e) Date: Mar. 23, 1995
[87] PCT Pub. No.: WO93/20745
  PCT Pub. Date: Oct. 28, 1993

[30] Foreign Application Priority Data

Apr. 22, 1992 [NL] Netherlands ............... 9200731

[51] Int. Cl.$^6$ ............................................. A61B 5/00
[52] U.S. Cl. ............................. 600/309; 600/584
[58] Field of Search ......................... 128/630, 632, 128/635, 637, 760, 771

[56] References Cited

U.S. PATENT DOCUMENTS

| | | |
|---|---|---|
| 3,649,199 | 3/1972 | Littlejohn . |
| 4,274,417 | 6/1981 | Delpy ............................ 128/632 |
| 4,311,789 | 1/1982 | Nylen et al. . |
| 4,516,580 | 5/1985 | Polanyi ............................ 128/632 |
| 4,586,149 | 4/1986 | Stillman et al. .................. 128/635 |
| 4,756,314 | 7/1988 | Eckenhoff et al. ............... 128/760 |
| 5,050,604 | 9/1991 | Reshef et al. .................... 128/632 |

FOREIGN PATENT DOCUMENTS

| | | |
|---|---|---|
| 0 453 383A1 | 10/1991 | European Pat. Off. . |
| 28 49 973A1 | 5/1980 | Germany . |
| 1581338 | 12/1980 | United Kingdom ............ 128/632 |

OTHER PUBLICATIONS

Lo et al., "Transepidermal Potassium Ion, Chloride Ion, and Water Fluxacross Delipidized and Cellophane Tape-Stripped Skin," Dermatologica, 1990, v. 180, pp. 66–68.

Websters II New Riverside University Dictionary, The Riverside Publishing Company, 1994, p. 550.

*Primary Examiner*—Jennifer Bahr
*Assistant Examiner*—Bryan K. Yarnell
*Attorney, Agent, or Firm*—Fitch, Even, Tabin & Flannery

[57] ABSTRACT

For non-invasively monitoring the concentration of a substance in blood, use is made of a pickup unit, with a cavity through which a liquid is passed. The cavity is held against the skin and the concentration of the substance which has penetrated into the passing liquid is measured. The method according to the invention makes it possible to monitor non-invasively and continuously the extent to which various low-molecular, water-soluble substances are present in the body of a human or an animal. Further described is an instrument for carrying out the method according to the invention.

21 Claims, 1 Drawing Sheet

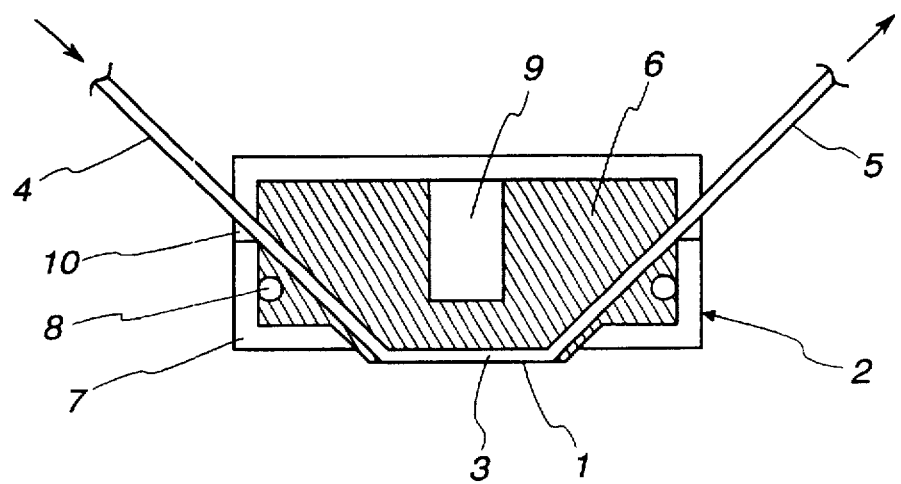

NON-INVASIVE MONITORING OF A CONSTITUENT OF A PHYSIOLOGICAL FLUID

BACKGROUND OF THE INVENTION

The invention relates to a method for non-invasively monitoring the concentration of a substance in a fluid produced by a human or an animal, in which method a pickup unit is held against the skin and the amount of substance received in the pickup unit is measured.

Such a method is disclosed in Japanese patent application 61-25541. This known method is intended for measuring the glucose concentration in the blood, in particular in patients with diabetes.

It is observed that hereinafter the term "patient" is understood to mean a human or an animal in general, whether healthy or ill.

According to this known method, a glucose oxidase enzyme is immobilized directly behind a cellulose membrane which has a good permeability to water and substances dissolved therein. Behind that, a limiting membrane is provided, which arrests reduced substances but allows water, hydrogen peroxide and salts to pass therethrough. Behind this membrane, hydrogen peroxide is detected with a platinum electrode.

The glucose oxidase enzyme produces hydrogen peroxide and an acid, depending on the amount of glucose which has passed through the cellulose membrane. The acid is arrested by the limiting membrane, but the hydrogen peroxide is allowed to pass. Through the electrode flows an electrical current which is dependent on the amount of hydrogen peroxide which has entered the fluid. Thus, on the basis of the current intensity, the amount of glucose which has passed through the cellulose membrane can be determined. The amount of glucose which has passed through the cellulose membrane, in turn, is dependent on the glucose concentration in the blood. Thus, this concentration can be monitored continuously and without A drawback of this known method is that it is only suitable for monitoring the glucose concentration.

In other known methods where, on the basis of the substance penetrating through the skin, the extent to which that substance is present in the body is measured transcutaneously, that substance is accumulated over a given period. An interruption of the accumulation or an unreliable period within the time period of the accumulation is then disastrous for the reliability of the results obtained after that interruption or unreliable period.

SUMMARY OF THE INVENTION

The object of the invention is to provide a method which is also suitable for non-invasively monitoring the concentration of other low-molecular, water-soluble substances.

According to the present invention, this object is realized in that, in a method of the type described in the opening paragraph hereof, liquid is passed through the pickup unit continuously and the concentration of the substance is measured in the liquid stream, downstream of the pickup unit.

In the method according to the invention any accumulation of the substances received in the liquid is avoided in that the liquid is continuously refreshed. As a result, regardless of the duration of the monitoring, as long as the concentration of the substance in question, for instance in the blood, remains within a given range, the concentration in the liquid of the substance whose concentration in the blood is to be monitored will remain within a corresponding, relatively limited range. This range can moreover be influenced by appropriately choosing the replacement rate of the liquid in the cavity. Thus, the concentration of the substance in question in the liquid can be caused to remain within a range within which it can be properly measured.

Further, the concentration of the substance in question in the liquid is to a high degree directly proportional to the concentration of that substance in the blood. Thus, the course of the concentration of the substance in the liquid provides in a simple manner an indication of the course of the concentration of that substance in the blood. Interruption of the measurements or periods within the time duration of the monitoring which are considered unreliable have no or hardly any adverse influence on the reliability of the results obtained after that interruption or unreliable period.

The method according to the invention is suitable inter alia for monitoring the concentration in the blood of substances which are not removed from the liquid during measurement. In principle, the concentration in the blood of any low-molecular substance can be monitored and the method according to the invention can be used for monitoring the concentration of both metabolic substances and medicaments.

The method according to the invention is suitable not only for measuring the concentration of substances in the blood but also for measuring the concentration in other fluids in the body or secreted by the body, such as sweat or epidermal moisture.

A further advantage of the method according to the invention is that the substance to be measured itself penetrates into the liquid and can be detected. As a consequence, a retarding, interfering and complicating intermediate conversion step such as the step utilized in the known method, whereby hydrogen peroxide is produced by the glucose oxidase enzyme, can in most cases be omitted.

The invention can further be embodied in an instrument adapted for the application of the method according to the invention, and in a pickup unit for use in a device according to the invention.

BRIEF DESCRIPTION OF THE FIGURE

FIG. 1 is an embodiment of the pickup unit for use in a device according to the invention.

DESCRIPTION OF THE PREFERRED EMBODIMENTS

The exemplary embodiment of a pickup unit as shown in longitudinal section in the drawing, for use in an instrument for carrying out the method according to the invention, comprises a membrane 1 and a housing 2 with a cavity 3 closed off by the membrane 1. For discharging liquid located behind the membrane 1 and for supplying new liquid behind the membrane 1, the pickup unit comprises a supply conduit 4 and a discharge conduit 5, respectively. Means for measuring the concentration of a substance in liquid discharged from the cavity 3 are not shown. These may for instance be arranged at a distance from the pickup unit in the discharge conduit 5.

For carrying out the method according to the invention, the membrane 1 of the pickup unit is positioned and retained against the skin of a patient. Various substances penetrate both through the skin of the patient and through the membrane 1 and are dissolved in the liquid passing behind and along the membrane 1 through the cavity 3. The liquid is discharged from the cavity 3 and new liquid is supplied, whilst in similar manner substances originating from the blood penetrate into and are dissolved in the new liquid. The concentration of the substance or substances whose concentration in the blood is to be monitored is always measured in the discharged liquid.

Because in the method according to the invention the liquid in the cavity 3 is continuously replaced, no excessive accumulation of substances which have passed through the mebrane 1 occurs, even if the duration of monitoring is prolonged. As a result, regardless of the duration of monitoring, as long as the concentration of the substance in question in the blood remains within a given expectable range, the concentration in the liquid of the substance whose concentration in the blood is to be monitored, will remain within a corresponding, relatively limited range. This range can moreover be influenced by appropriately choosing the replacement rate of the liquid behind the membrane 1 in relation to the effective area of the membrane 1. Thus, the concentration of the substance in question in the liquid can be caused to remain within a range within which it can be properly measured.

Further, the concentration of a substance can be monitored continuously without entailing any additional delay of the observation owing to the necessity of waiting for a measuring interval to elapse.

A further advantage of passing the liquid along the membrane continuously is that the liquid behind the membrane is kept moving continuously, which improves the mixing of the substances in the liquid which have penetrated into the cavity 3.

Because accumulation of substances in the cavity 3 is limited, the method according to the invention is suitable for monitoring the concentration in the blood of substances which are not removed from the liquid during measurement. Moreover, it is possible to measure the concentration of several substances simultaneously using a single pickup unit by measuring the concentration of several substances in the liquid. For that purpose, it is for instance possible to arrange sensors of several measuring means in the discharge conduit 5. By arranging the sensors in the discharge conduit any problems with regard to space, which would occur upon their arrangement in the cavity 3, are solved.

The measured concentration of the substance in the liquid is to a high degree proportional to the concentration of that substance in the blood some time prior to the time of measurement of the concentration of that substance in the liquid. The duration of that time is determined by the average time which it takes a particle of that substance to move from the blood stream to the means for determining the concentration in the discharged liquid.

Because the liquid behind the membrane is continuously replaced and the concentration in this liquid is measured after it has been discharged, the reliability of measuring results is not influenced by interruptions of the measurement or temporarily unreliable periods during the period of monitoring.

A further advantage of the method according to the invention is that the substances to be measured themselves penetrate into the liquid, whereafter that liquid is discharged and the concentration of those substances in the discharge liquid is measured. This makes it possible, in most cases, to dispense with a retarding, interfering and complicating intermediate conversion step. The concentration in the liquid of lactate, ethanol and glucose can for instance be measured by means of measuring methods which are known per se for microdialysis, such as lactography for following the lactate concentration, detecting NADH or NADPH produced by enzymes for following the concentration of ethanol and glucose, and detecting $H_2O_2$ for following the choline concentration. Such measuring methods are for instance known from "On-line real time monitoring of extracellular lactate, ethanol, glucose and choline, using microdialysis and enzyme reactors" by Korf et al. (1991) in "Microdialysis in the Neurosciences" T. E. Robinson and J. B. Justice (eds.), Elsevier Science Publishers B.V. 1991 and in "Continuous monitoring of the extracellular lactate concentration by microdialysis for the study of rat muscle metabolism in vivo", by De Boer et al. (1991) in the European Journal of Physiology, 419: 1–6, which publications are hereby referred to. The concentration of some substances can be monitored directly in electrochemical manner.

Because the means for supplying and discharging the liquid are constructed as supply and discharge conduits 4 and 5 connecting to the cavity 3, liquid can be continuously passed along the membrane 1 in a simple manner. The concentration of a substance can be measured downstream of the cavity 3 in the liquid stream.

The cavity 3 is constructed as a groove in the housing 2 and forms a channel, one end thereof connecting to the supply conduit 4 and the other end connecting to the discharge conduit 5. This makes it possible to manufacture the housing 2 with cavity 3 in a simple manner. Further, as a result, the cavity has a small volume, which in turn is advantageous for a fast reaction of the concentration in the liquid to the supply of substances through the membrane 1. Because the channel is elongated in the direction of transport, comparatively little mixing occurs in the direction of flow, which is advantageous for the measuring sensitivity.

The groove of the cavity 3 preferably has a width which is greater than its depth. As a result, a relatively large effective passage area in contact with the skin is obtained and little mixing of the liquid is required to obtain a homogeneous distribution over the cross-section of the channel-shaped cavity 3, of the substances which have passed through the membrane 1 into the liquid.

The means for measuring the concentration of a substance in liquid discharged from behind the membrane 1 are preferably arranged for measuring the concentration in the discharge conduit 5. Thus, a fast reaction of the measured value to changes in the concentration in the liquid is obtained. Moreover, as a consequence, the measuring methods as described hereinabove can be employed, which methods are particularly suitable for the continuous measurement of concentrations in a flowing liquid.

The housing 2 comprises a base body 6 and a cap 7, the membrane 1 being clamped between the base body 6 and the cap 7. In this way, in a simple manner provisions have been created for fixing the membrane 1. The membrane can be removed in a simple manner to replace it by a new membrane. It is desirable to replace the membrane after each use because protracted intensive contact of the membrane with the skin of consecutive patients would involve a substantial risk of contamination of a patient by a preceding patient.

On the side opposite the membrane 1, the pickup unit is provided with a cover 10 with apertures for the supply and the discharge conduits (4 and 5, respectively).

The cap 7 and the base body 6 can be readily cleaned and optionally sterilized. The base body 6 comprises a circumferential groove in which rests an O-ring 8. When the cap 7 is arranged over the base body 6, this O-ring 8 provides a seal between the cap 7 and the base body 6. The cap 7 is provided with an opening through which projects a portion of the base body 6 that comprises the cavity 3. The membrane 1 rests inter alia against this portion of the base body 6, so that in use the portion of the membrane 1 that is located in front of the cavity 3 is reliably pressed against the skin.

The pickup unit is provided with a thermostatically controlled source of heat 9. The source of heat 9 can for instance comprise a resistor as energy converter and a temperature-dependent semiconductor as thermostat. The base body 6 is preferably made from a material that conducts heat well, such as aluminum or silver. Examples of suitable materials for other parts of the housing 2 include synthetic material or aluminum.

By means of the source of heat 9, the skin can be heated to a constant temperature in the region of the membrane 1. According as the skin is warmer, capillary loops under the skin open up further and more arterial blood flows through them, which promotes the penetration of substances from the arterial blood through the skin. By heating the skin to a constant temperature, this effect can be promoted and controlled, which promotes the reliability of the relationship between the substances penetrating through the skin and the concentrations thereof in the arterial blood.

To render the skin rich in blood, on the one hand, and to avoid burns, on the other, the skin in the region of the membrane is preferably heated to a temperature between 40° and 45° C. In most cases, a temperature of 42° C. offers the best compromise.

For measuring the concentration of an acid, such as lactate, the liquid is preferably passed through the cavity 3 at a rate of flow between 0.025 and 15 µl/min per mm² of passage area of the cavity, proximal to the skin. Good results are for instance obtained when a cavity of a depth of 0.1 to 0.2 mm, a width of 0.5 mm and a length of 8 mm is used and the rate of flow of liquid passed through the cavity 3 is approx. 10 µl/min. Because the cavity is wider than its depth, at a given volume of the cavity a relatively large effective passage area is obtained and relatively little mixing of that liquid is necessary to obtain a homogeneous distribution within the liquid of substances which have passed through the membrane.

A rate of flow similar to that for measuring the concentration of an acid, such as lactate, is preferred for measuring the concentrations of more lipophilic substances, such as ethanol.

For measuring the concentration of hydrophilic substances, such as glucose, the liquid is preferably passed through the cavity at a lower rate of flow, viz., between 0.025 and 15 µl/min per mm² of passage area of the cavity proximal to the skin. In the case of a pickup unit with an effective membrane area as described hereinabove, a very suitable rate of flow is for instance 2.5 µl/min.

Prior to measurement, the skin is preferably treated by applying a sticky material thereto at least once and subsequently stripping this from the skin. This technique is known by the name of "cellulose stripping" and for instance described in "Transepidermal potassium ion, chloride ion and water flux across delipidized and cellophane tape stripped skin" by Lo et al. in Dermatologica, 1990.

According to this technique, the horny layer of the epidermis of the skin is partly removed, so that the barrier action of the skin is reduced. In the case of glucose and alcohol, for instance, this yields an increase of the flow of substances passing through the skin by a factor of between 5 and 20. This makes it possible, utilizing a relatively small passage area of the cavity 3 proximal to the skin and a relatively high replacement rate of liquid, to yet obtain concentrations of the substance(s) to be monitored in the liquid that fall within a range within which they can be properly measured. Further, through the reduced barrier action of the skin, the influence of this action on the amounts of substances penetrating into the liquid is limited, which is advantageous for the predictive value of the measured concentration(s) of that substance or those substances in the liquid.

It is observed that, if so desired, other methods for limiting the barrier action of the skin can be used as well, such as cleansing the skin with the aid of a fat-dissolving and/or abrasive substance or by the use of penetration-promoting agents such as Dimethyl Sulfoxide (sometimes referred to as DMSO) or Laurocapram (available under the brand name Azone).

The liquid which is used is preferably a physiological liquid. This provides the advantage that the concentration of virtually any substance capable of passing through the skin can be measured therein.

The pickup unit can for instance be fitted against a dorsal part of the lower arm. Depending on the objective of the measurements, the membrane can naturally be arranged against another part of the body. Prior to the arrangement of the pickup unit, a surface of, for instance, 2×2 cm of the skin is treated by repeatedly sticking a self-adhesive foil to it. In the pickup unit, for instance a cellulose membrane of a thickness of 25 µm can be arranged. Such a membrane is commercially available, for instance from A. H. Thomas Co. in Philadelphia, Pa., USA. The pickup unit with the membrane is subsequently fitted against the skin. For that purpose, it is for instance possible to use a double-sided self-adhesive tape. This is commercially available, for instance from Draeger in Zoetermeer, The Netherlands.

After the pickup unit has been fitted as described hereinabove, it is preferably heated and physiological liquid is passed through the pickup unit, the concentration of one or more substances in the liquid being measured downstream of the pickup unit. If, in addition to the variation in the concentration, the absolute concentration of a substance in the blood is to be monitored as well, preferably the ratio between the concentration of that substance in the liquid and that in the blood is established by taking one or more blood samples and assaying the concentration of that substance in that blood sample. The fact is that although this ratio has been found to be substantially constant for most substances for a particular individual, it may vary from one person to another.

If the pickup unit is heated, it should be moved after 6–8 hour intervals, so as prevent skin burns.

The invention can for instance be used for monitoring the lactate concentration in the blood of patients who are seriously ill, so as to avoid repeated venal puncture, for monitoring the glucose concentration in the blood of newborn babies in intensive care, or for non-invasively monitoring arterial concentrations, such as the lactate concentration within the framework of sports physiology.

The invention can further be used for continuously monitoring the concentration of a medicament in a patient. On-line monitoring even makes it possible to administer medicament automatically upon a decrease of concentration, so as to keep the concentration at a given level and to minimize temporary overdosing with any associated additional harmful side-effects.

The use of the membrane 1 is advantageous because thereby in a simple manner a reliable seal of the cavity 3 is obtained, so that the liquid passed therethrough cannot leak away. Further, through the use of the membrane 1, the skin is to a lesser extent subject to contact with the liquid, which is advantageous in particular in the case of measurements over very long periods of time. Further, through the choice of a suitable membrane, a selection of substances penetrating into the cavity 3 can be obtained. Finally, through the membrane 1, contamination of downstream parts of the measuring instrument according to the invention can be avoided.

It is also possible, however, to arrange for the cavity 3 to bound the skin directly without interposition of a membrane. In that case, no membrane is required, so that costs are saved, and the amount of substances penetrating into the cavity is generally larger than in the case where a membrane is provided between the cavity 3 and the skin, so that these substances will normally be easier to measure. The use of a pickup unit without membrane 1 is particularly attractive if measurements of relatively short duration are involved, where a short reaction time is desired (and therefore a high replacement rate) and/or where it is problematic to obtain sufficiently high concentrations of the substance to be measured in the liquid passed through the cavity 3, if a membrane 1 is used.

We claim:

1. A method for non-invasively monitoring the concentration of a substance in a liquid produced by a human or an animal, comprising steps of holding a cavity of a pickup unit against the skin, measuring the amount of substance received in the pickup unit, continuously passing a liquid stream through the pickup unit and measuring the concentration of the substance in the continuous liquid stream downstream of the cavity.

2. A method according to claim 1 comprising, prior to measurement, treating the skin by applying an adhesive material thereto at least once and subsequently stripping this from the skin.

3. A method according to claim 1 comprising, heating skin in the region of the cavity to a constant temperature.

4. A method according to claim 3, wherein said temperature is between 40° and 45° C.

5. A method according to claim 1, wherein the liquid is a physiological liquid.

6. An instrument for carrying out the method according to claim 1, comprising a cavity to which connect a supply and a discharge conduit, means for passing a liquid stream through the cavity, and means located downstream of the cavity, for measuring the concentration of a substance in the liquid stream in said discharge conduit.

7. An instrument according to claim 6, wherein the cavity is designed as a groove and forms a channel in the condition where it is closed off by a membrane, one end of said channel connecting to the supply conduit and the other end connecting to the discharge conduit.

8. An instrument according to claim 7, wherein the groove has a width greater than its depth.

9. An instrument according to claim 6, wherein the pickup unit comprises a thermostatically controlled source of heat.

10. An instrument according to claim 6, wherein the cavity is designed as a groove and forms a channel in the condition where it is closed off by the skin, one end of said channel connecting to the supply conduit and the other end connecting to the discharge conduit.

11. A method for non-invasively monitoring the concentration of a substance in a liquid produced by a human or an animal by a pickup unit comprising a cavity bounded by a membrane, comprising the steps of holding the cavity of the pickup unit against the skin so that the membrane is against the skin, measuring the amount of substance received in the pickup unit through the membrane, continuously passing a liquid stream through the pickup unit and measuring the concentration of the substance in the liquid stream downstream of the cavity.

12. An instrument for carrying out the method according to claim 11, comprising a cavity to which connect a supply and a discharge conduit, means for passing a liquid through the cavity, and means located downstream of the cavity, for measuring the concentration of a substance in the liquid stream, wherein the cavity is closed off by the membrane.

13. An instrument according to claim 12, wherein the means for measuring the concentration of a substance in the liquid stream downstream of the cavity is arranged for measuring the concentration in the discharge conduit.

14. A pickup unit for use in an instrument according to claim 12, comprising a cavity, to which connect a supply and a discharge conduit and a contacting surface around the cavity to be held against the skin in its entirety, wherein the cavity is closed off by a membrane.

15. An instrument according to claim 12, wherein the cavity is designed as a groove and forms a channel in the condition where it is closed off by the membrane, one end of said channel connecting to the supply conduit and the other end connecting to the discharge conduit.

16. An instrument for carrying out the method according to claim 11, comprising a cavity to which connect a supply and a discharge conduit, means for passing a liquid through the cavity, and means located downstream of the cavity, for measuring the concentration of a substance in the liquid stream, wherein the cavity is closed off by a membrane, and wherein the pickup unit comprises a base body and a cap, the membrane being clamped between the base body and the cap.

17. A pickup unit for use in an instrument according to claim 16, comprising a base body with a cavity, to which connect a supply and a discharge conduit, a cap, a membrane closing off the cavity and a contacting surface around the membrane, wherein the membrane is clamped between the base body and the cap.

18. A method for non-invasively monitoring the concentration of a substance in a liquid produced by a human or an animal, comprising the steps of holding a pickup unit against the skin, measuring the amount of substance received in the pickup unit, passing liquid through the pickup unit continuously at a rate of flow between 0.025 and 15 µl/min per $mm^2$ of effective area of contact with the skin, and measuring the concentration of the substance in the liquid stream downstream of the cavity.

19. A method according to claim 18, wherein the concentration of an acid is measured.

20. A method according to claim 18, wherein the concentration of a lipophilic substance is measured.

21. A method according to claim 18, wherein the concentration of a hydrophilic substance is measured.

* * * * *